US006333302B1

(12) United States Patent
Beer et al.

(10) Patent No.: US 6,333,302 B1
(45) Date of Patent: Dec. 25, 2001

(54) **USE OF HYPERSENSITIVE RESPONSE ELICITOR PROTEIN OR POLYPEPTIDE FROM *CLAVIBACTER MICHIGANENSIS* FOR DISEASE RESISTANCE, GROWTH ENHANCEMENT AND INSECT CONTROL**

(75) Inventors: Steven V. Beer, Ithaca, NY (US); Jerry L. Butler, Woodinville, WA (US)

(73) Assignees: Cornell Research Foundation, Inc., Ithaca, NY (US); Eden Bioscience Corporation, Bothell, WA (US)

( * ) Notice: Subject to any disclaimer, the term of this patent is extended or adjusted under 35 U.S.C. 154(b) by 0 days.

(21) Appl. No.: 09/136,625

(22) Filed: Aug. 19, 1998

Related U.S. Application Data
(60) Provisional application No. 60/057,464, filed on Sep. 3, 1997.

(51) Int. Cl.[7] ............... A01N 63/00; A01N 37/18; C12N 5/00

(52) U.S. Cl. ............... 514/2; 424/93.4; 435/430

(58) Field of Search ............... 514/2; 424/93.4; 435/430

(56) References Cited

U.S. PATENT DOCUMENTS

| | | | |
|---|---|---|---|
| 4,569,841 | 2/1986 | Liu | 424/93 |
| 4,597,972 | 7/1986 | Taylor | 426/36 |
| 4,601,842 | 7/1986 | Caple et al. | 252/70 |
| 4,740,593 | 4/1988 | Gonzalez et al. | 425/243 |
| 4,851,223 | 7/1989 | Sampson | 424/711 |
| 4,886,825 | 12/1989 | Ruess et al. | 514/383 |
| 4,931,581 | 6/1990 | Schurter et al. | 560/18 |
| 5,057,422 | 10/1991 | Bol et al. | 435/240.4 |
| 5,061,490 | 10/1991 | Paau et al. | 424/93 |
| 5,135,910 | 8/1992 | Blackburn et al. | 514/2 |
| 5,173,403 | 12/1992 | Tang et al. | 435/6 |
| 5,217,950 | 6/1993 | Blackburn et al. | 514/2 |
| 5,243,038 | 9/1993 | Ferrari et al. | 536/23.1 |
| 5,244,658 | 9/1993 | Parke | 504/117 |
| 5,260,271 | 11/1993 | Blackburn et al. | 514/2 |
| 5,348,743 | 9/1994 | Ryals et al. | 424/94.61 |
| 5,494,684 | 2/1996 | Cohen | 424/523 |
| 5,523,311 | 6/1996 | Schurter et al. | 548/361 |
| 5,550,228 | 8/1996 | Godiard et al. | 536/24.1 |
| 5,552,527 | 9/1996 | Godiard et al. | 530/379 |
| 5,650,387 | 7/1997 | Wei et al. | 514/2 |
| 5,708,139 | 1/1998 | Collmer et al. | 530/350 |

FOREIGN PATENT DOCUMENTS

| | | |
|---|---|---|
| 0 589 110 | 3/1994 | (EP). |
| WO 88/09114 | 12/1988 | (WO). |
| WO 90/13224 | 11/1990 | (WO). |
| WO 91/10363 | 7/1991 | (WO). |
| WO 94/01546 | 1/1994 | (WO). |
| WO 94/26782 | 11/1994 | (WO). |
| WO 95/19443 | 7/1995 | (WO). |
| WO 96/39802 | 12/1996 | (WO). |

OTHER PUBLICATIONS

Gitaitis, Plant Disease, vol. 74, No. 1, pp. 58–60, Jan. 1990.*
Chemical Abstracts 120(15):184202 (1994), Lampel et al., "Integrative Cloning, Expression, and Stability of the cryIA(c) Gene from *Bacillus thuringiensis* subsp. *kustaki* in a Recombinant Strain of *Clavibacter xyli* subsp. *cynodontis*," *Appl. Environ. Microbiol.* 60(2):501–508 (1994).
Chemical Abstract 127(4):47639 (1997), Metzler et al., "The Status of Molecular Biological Research on the Plant Pathogenic Genus Clavibacter," *FEMS Microbiol. Lett.* 150(1):1–8 (1997).
Biological Abstracts 95:452043 (1995), Tomasino et al., "Field Performance of *Clavibacter xyli* subsp. *cynodontis* Expressing the Insecticidal Protein Gene cryIA(c) of *Bacillus thuringiensis* Against European Corn Borer in Field Corn," *Biological Control* 5(3):442–448 (1995).
Biological Abstracts 95:350265 (1997), Nissinen et al., "*Clavibacter michiganensis* subsp. *sepedonicus* Elicits a Hypersensitive Response in Tobacco and Secretes a Hypersensitive Response–inducing Protein," *Phytopathol.* 87(7):678–684.
Nissinen et al., "*Clavibacter michiganensis* subsp. *sepedonicus* Elicits a Hypersensitive Response in Tobacco and Secretes Hypersensitive Response–Inducing Protein(s)," *Phytopathology*, 87(7):678–684 (1997).
Collmer et al., "*Erwinia chrysanthemi* and *Pseudomonas syringae*: Plant Pathogens Trafficking in Extracellular Virulence Proteins," pp. 43–78.
Wei et al., "Proteinaceous Elicitor of the Hypersensitive Response from *Xanthomonas Campestris* PV. Glycines," Seventh Internat'l Symposium on Molecular Plant Microbe Interactions, Abstract No. 244 (Jun. 1994).
Preston et al. "The HrpZ Proteins of *Pseudomonas syringae* pvs. *syringae, glycinea,* and *tomato* Are Encoded by an Operon Containing *Yersinia ysc* Homologs and Elicit the Hypersensitive Response in Tomato but not Soybean," *MPMI*, 8(5):717–732 (1995).
Bauer et al., "*Erwinia chrysanthemi hrp* Genes and Their Involvement in Elicitation of the Hypersensitive Response In Tobacco," Seventh Internat'l Symposium on Molecular Plant Microbe Interactions, Abstract No. 146 ("Abstract").

(List continued on next page.)

*Primary Examiner*—David M. Naff
*Assistant Examiner*—Mike Meller
(74) *Attorney, Agent, or Firm*—Nixon Peabody LLP

(57) ABSTRACT

The present invention is directed to the use of a protein or polypeptide from Gram positive bacteria, such as *Clavibacter michiganensis* subsp. *sepedonicus*, which elicits a hypersensitive response in plants. This protein or polypeptide can used to impart disease resistance to plants, to enhance plant growth, and/or to control insects on plants. This can be achieved by applying the hypersensitive response elicitor protein or polypeptide in a non-infectious form to plants or plant seeds under conditions where the protein or polypeptide contacts the cells of the plant or the plant seed and is effective to impart disease resistance, to enhance plant growth, and/or to control insects on plants or plants grown from the plant seeds.

12 Claims, No Drawings

OTHER PUBLICATIONS

Bauer et al., "*Erwinia chrysanthemi* Harpin$_{ecch}$: An Elicitor of the Hypersensitive Response that Contributes to Soft–Rot Pathogenesis," *MPMI*, 8(4):484–491 (1995).

Huang et al., "Characterization of the hrp Cluster from *Pseudomonas syringae* pv. *syringae* 61 and TnphoA Tagging of Genes Encoding Exported or Membrane–Spanning Hrp Proteins," *Molecular Plant–Microbe Interactions*, 4(5):469–476 (1991).

Huang et al., "The *Pseudomonas syringae* pv. syringae 61 hrpH Product, an Envelope Protein Required for Elicitation of the Hypersensitive Response in Plants," *Journal of Bacteriology*, 174(21):6878–6885 (1992).

Bonas, U., "hrp Genes of Phytopathogenic Bacteria," *Current Topics in Microbiology and Immunology*, 192:79–98 (1994).

Bauer et al., "Cloning of a Gene from *Erwinia amylovora* Involved in Induction of Hypersensitivity and Pathogenicity," Sixth International Conference on Plant Pathogenic Bacteria, (Jun. 2–7, 1985).

Wei et al., "Induction of Systemic Resistance with Seed Treatment by PGPR Strains," pp. 191–194.

Laby et al., "Structural and Functional Analysis of *Erwinia amylovora* Harpin, An Elicitor of the Plant Hypersensitive Response," *Phytopathology* 84:345 (1994).

Huang et al., "Molecular Cloning of a *Pseudomonas syringae* pv. *syringae* Gene Cluster that Enables *Pseudomonas fluorescens* to Elicit the Hypersensitive Response in Tobacco Plants," *Journal of Bacteriology*, 170:4748–4756 (1988).

Bauer et al., "*Erwinia chrysanthemi* hrp Genes and Their Involvement in Soft Rot Pathogenesis and Elicitation of the Hypersensitive Response," *MPMI*, 7(5):573–581 (1994).

Steinberger et al., "Creation and Complementation of Pathogenicity Mutants of *Erwinia amylovora*," *Molecular Plant–Microbe Interations*, 1(3):135–144 (1988).

Beer et al., "The Hypersensitive Response is Elicited by *Escherichia coli* Containing a Cluster of Pathogenicity Genes from *Erwinia amylovora*," *Phytopathology* 79(10):Abstract No. 169 (Aug. 1989).

Laby et al., "Cloning and Preliminary Characterization of an HRP Gene Cluster of *Erwinia amylovora*," *Phytopathology* 79(10):Abstract No. 607 (Aug. 1989).

Bauer et al., "Further Characterization of an hrp Gene Cluster of *Erwinia amylovora*," *Molecular Plant–Microbe Interations*, 4(5):493–499 (1991).

Beer et al., "The HRP Gene Cluster of *Erwinia amylovora*," Advances in Molecular Genetics of Plant–Microbe Interactions 1:53–60 (1991).

Beer et al., "Are Harpins Universal Elicitors of the Hypersensitive Response of Phytopathogenic Bacteria?" Advances in Molecular Genetics of Plant–Microbe Interactions 2:281–286 (1992).

Laby et al., "Hybridization and Functional Complementation of the hrp Gene Cluster from *Erwinia amylovora* Strain Ea321 with DNA of Other Bacteria," *Molecular Plant–Microbe Interactions*, 5(5):412–419 (1992).

Wei et al., "Harpin, Elicitor of the Hypersensitive Response Produced by the Plant Pathogen *Erwinia amylovora*," *Science*, 257:85–88 (1992).

He et al., "*Pseudomonas syringae* pv. syringae Harpin$_{Pss}$: A Protein That Is Secreted Via the Hrp Pathway and Elicits The Hypersensitive Response in Plants," *Cell*, 73:1255–1266 (1993).

Bogdanove et al., "Unified Nomenclature for Broadly Conserved hrp Genes of Phytopathogenic Bacteria," *Molecular Microbiology*, 20(3):681–683 (1996).

Wei et al., "Induced Systemic Resistence to Cucumber Diseases and Increased Plant Growth by Plant Growth–Promoting Rhizobacteria Under Field Conditions," *Phytopathology* 86:221–224 (1996).

Qiu et al., Abstract: "Treatment of Tomato Seed with Harpin Enhances Germination and Growth and Induces Resistance in Ralstonia solanacearum," *Phytopathology*, 87(6):580 (1997).

* cited by examiner

USE OF HYPERSENSITIVE RESPONSE ELICITOR PROTEIN OR POLYPEPTIDE FROM *CLAVIBACTER MICHIGANENSIS* FOR DISEASE RESISTANCE, GROWTH ENHANCEMENT AND INSECT CONTROL

This application claims benefit of U.S. Provisional Patent Application Ser. No. 60/057,464, filed Sep. 3, 1997.

FIELD OF THE INVENTION

The present invention relates to the use of the hypersensitive response elicitor from Gram positive bacteria, such as *Clavibacter michiganensis* subsp. *sepedonicus*, for disease resistance, growth enhancement, and insect control.

BACKGROUND OF THE INVENTION

Interactions between bacterial pathogens and their plant hosts generally fall into two categories: (1) compatible (pathogen-host), leading to intercellular bacterial growth, symptom development, and disease development in the host plant; and (2) incompatible (pathogen-nonhost), resulting in the hypersensitive response, a particular type of incompatible interaction occurring, without progressive disease symptoms. During compatible interactions on host plants, bacterial populations increase dramatically and progressive symptoms occur. During incompatible interactions, bacterial populations do not increase, and progressive symptoms do not occur.

The hypersensitive response ("HR") is a rapid, localized necrosis that is associated with the active defense of plants against many pathogens (Kiraly, Z., "Defenses Triggered by the Invader: Hypersensitivity," pages 201–224 in: *Plant Disease: An Advanced Treatise*, Vol. 5, J. G. Horsfall and E. B. Cowling, ed. Academic Press New York (1980); Klement, Z., "Hypersensitivity," pages 149–177 in: *Phytopathogenic Prokaryotes*, Vol. 2, M. S. Mount and G. H. Lacy, ed. Academic Press, New York (1982)). The hypersensitive response elicited by bacteria is readily observed as a tissue collapse if high concentrations ($\geq 10^7$ cells/ml) of a limited host-range pathogen like *Pseudomonas syringae* or *Erwinia amylovora* are infiltrated into the leaves of nonhost plants (necrosis occurs only in isolated plant cells at lower levels of inoculum) (Klement, Z., "Rapid Detection of Pathogenicity of Phytopathogenic Pseudomonads," *Nature* 199:299–300; Klement, et al., "Hypersensitive Reaction Induced by Phytopathogenic Bacteria in the Tobacco Leaf," *Phytopathology* 54:474–477 (1963); Turner, et al., "The Quantitative Relation Between Plant and Bacterial Cells Involved in the Hypersensitive Reaction," *Phytopathology* 64:885–890 (1974); Klement, Z., "Hypersensitivity," pages 149–177 in *Phytopathogenic Prokaryotes*, Vol. 2., M. S. Mount and G. H. Lacy, ed. Academic Press, New York (1982)). The capacities to elicit the hypersensitive response in a nonhost and be pathogenic in a host appear linked. As noted by Klement, Z., "Hypersensitivity," pages 149–177 in *Phytopathogenic Prokaryotes*, Vol. 2., M. S. Mount and G. H. Lacy, ed. Academic Press, New York, these pathogens also cause physiologically similar, albeit delayed, necroses in their interactions with compatible hosts. Furthermore, the ability to produce the hypersensitive response or pathogenesis is dependent on a common set of genes, denoted hrp (Lindgren, P. B., et al., "Gene Cluster of *Pseudomonas syringae* pv. 'phaseolicola' Controls Pathogenicity of Bean Plants and Hypersensitivity on Nonhost Plants," *J. Bacteriol.* 168:512–22 (1986); Willis, D. K., et al., "hrp Genes of Phytopathogenic Bacteria," *Mol. Plant-Microbe Interact.* 4:132–138 (1991)). Consequently, the hypersensitive response may hold clues to both the nature of plant defense and the basis for bacterial pathogenicity.

The hrp genes are widespread in gram-negative plant pathogens, where they are clustered, conserved, and in some cases interchangeable (Willis, D. K., et al., "hrp Genes of Phytopathogenic Bacteria," *Mol. Plant-Microbe Interact.* 4:132–138 (1991); Bonas, U., "hrp Genes of Phytopathogenic Bacteria," pages 79–98 in: *Current Topics in Microbiology and Immunology: Bacterial Pathogenesis of Plants and Animals—Molecular and Cellular Mechanisms*, J. L. Dangl, ed. Springer-Verlag, Berlin (1994)). Several hrp genes encode components of a protein secretion pathway similar to one used by Yersinia, Shigella, and Salmonella spp. to secrete proteins essential in animal diseases (Van Gijsegem, et al., "Evolutionary Conservation of Pathogenicity Determinants Among Plant and Animal Pathogenic Bacteria," *Trends Microbiol.* 1:175–180 (1993)). In *E. amylovora*, *P. syringae*, and *P. solanacearum*, hrp genes have been shown to control the production and secretion of glycine-rich, protein elicitors of the hypersensitive response (He, S. Y., et al. "*Pseudomonas Syringae* pv. *Syringae* Harpin$_{Pss}$: a Protein that is Secreted via the Hrp Pathway and Elicits the Hypersensitive Response in Plants," *Cell* 73:1255–1266 (1993), Wei, Z.-H., et al., "HrpI of *Erwinia amylovora* Functions in Secretion of Harpin and is a Member of a New Protein Family," *J. Bacteriol.* 175:7958–7967 (1993); Arlat, M. et al. "PopA1, a Protein Which Induces a Hypersensitive-like Response on Specific Petunia Genotypes, is Secreted via the Hrp Pathway of *Pseudomonas solanacearum*," *EMBO J.* 13:543–553 (1994)).

The first of these proteins was discovered in *E. amylovora* Ea321, a bacterium that causes fire blight of rosaceous plants, and was designated harpin (Wei, Z.-M., et al, "Harpin, Elicitor of the Hypersensitive Response Produced by the Plant Pathogen *Erwinia amylovora*," *Science* 257:85–88 (1992)). Mutations in the encoding hrpN gene revealed that harpin is required for *E. amylovora* to elicit a hypersensitive response in nonhost tobacco leaves and incite disease symptoms in highly susceptible pear fruit. The *P. solanacearum* GMI1000 PopA1 protein has similar physical properties and also elicits the hypersensitive response in leaves of tobacco, which is not a host of that strain (Arlat, et al. "PopA1, a Protein Which Induces a Hypersensitive-like Response on Specific Petunia Genotypes, is Secreted via the Hrp Pathway of *Pseudomonas solanacearum*," *EMBO J.* 13:543–53 (1994)). However, *P. solanacearum* popA mutants still elicit the hypersensitive response in tobacco and incite disease in tomato. Thus, the role of these glycine-rich hypersensitive response elicitors can vary widely among gram-negative plant pathogens.

Other plant pathogenic hypersensitive response elicitors have been isolated, cloned, and sequenced. These include: *Erwinia chrysanthemi* (Bauer, et. al., "*Erwinia chrysanthemi* Harpin$_{Ech}$: Soft-Rot Pathogenesis," *MPMI* 8(4): 484–91 (1995)); *Erwinia carotovora* (Cui, et. al., "The RsmA$^-$ Mutants of *Erwinia carotovora* subsp. *carotovora* Strain Ecc71 Overexpress hrpN$_{Ecc}$ and Elicit a Hypersensitive Reaction-like Response in Tobacco Leaves," *MPMI* 9(7): 565–73 (1966)); *Erwinia stewartii* (Ahmad, et. al., "Harpin is not Necessary for the Pathogenicity of *Erwinia stewartii* on Maize," 8*th Int'l. Cong. Molec. Plant-Microb. Inter.* Jul. 14–19, 1996 and Ahmad, et. al., "Harpin is not Necessary for the Pathogenicity of *Erwinia stewartii* on Maize," *Ann. Mtg. Am. Phytopath. Soc.* Jul. 27–31, 1996); and *Pseudomonas syringae* pv. *syringae* (WO 94/26782 to Cornell Research Foundation, Inc.).

The present invention is directed to the use of a hypersensitive response elicitor protein or polypeptide from Gram positive bacteria.

SUMMARY OF THE INVENTION

The hypersensitive response eliciting protein or polypeptide from Gram positive bacteria, such as Clavibacter, particularly *Clavibacter michiganensis* subsp. *sepedonicus*, can be used to impart disease resistance to plants, to enhance plant growth, and/or to control insects. This involves applying the hypersensitive response elicitor protein or polypeptide in a non-infectious form to plants or plant seeds under conditions effective to impart disease resistance, to enhance plant growth, and/or to control insects on plants or plants grown from the plant seeds.

As an alternative to applying the gram positive hypersensitive response elicitor protein or polypeptide to plants or plant seeds in order to impart disease resistance, to enhance plant growth, and/or to control insects on plants, transgenic plants or plant seeds can be utilized. When utilizing transgenic plants, this involves providing a transgenic plant transformed with a DNA molecule encoding the hypersensitive response gram positive elicitor protein or polypeptide and growing the plant under conditions effective to impart disease resistance, to enhance plant growth, and/or to control insects in the plants or plants grown from the plant seeds. Alternatively, a transgenic plant seed transformed with the DNA molecule encoding the gram positive hypersensitive response elicitor protein or polypeptide can be provided and planted in soil. A plant is then propagated under conditions effective to impart disease resistance, to enhance plant growth, and/or to control insects on plants or plants grown from the plant seeds.

DETAILED DESCRIPTION OF THE INVENTION

The present invention relates to the use of the hypersensitive response elicitor protein or polypeptide from Gram positive bacteria, such as a Clavibacter, particularly *Clavibacter michiganensis* subsp. *sepedonicus,* for disease resistance, growth enhancement, and insect control in plants. This hypersensitive response elicitor protein or polypeptide is described in and can be isolated according to Nissinen, et al., "*Clavibacter michiganensis* subsp. *sepedonicus* Elicits a Hypersensitive Response in Tobacco and Secretes Hypersensitive Response-Inducing Protein(s)," *Phytopathology,* pp. 678–84 (1997), which is hereby incorporated by reference.

Identification of virulent strains, preparation and concentration of cell-free culture supernatants ("CCS") with elicitor activity, and partial purification of proteinaceous elicitor can be carried out according to the procedures set forth in Nissinen et al., "*Clavibacter michiganensis* subsp. *sepedonicus* Elicits a Hypersensitive Response in Tobacco and Secretes Hypersensitive Response-Inducing Protein(s)," *Phytopathology* 87(7):678–84 (1997).

Virulence of *C. michiganensis* subsp. *sepedonicus* strains was evaluated in potato (*Solanum tuberosum L.*), the only natural host, and eggplant (*S. melongene L.*), an artificial host commonly used as an indicator plant. Eggplants (cv. Black Beauty) that were 28-days old were grown in a greenhouse and inoculated by injecting stems at a single site with ~20 $\mu$l of bacterial suspension ($10^8$ cells per ml) in quarter-strength Ringer's solution (Zeller et al., *Phytopathol. Z.,* 112:198–206 (1985)). Daytime conditions were 24° C., with a 15-h photoperiod supplemented with sodium vapor lights, and the nighttime temperature was 19° C. Foliar wilt severity was rated 18 days after inoculation, using the 1 to 12 double-logarithmic Horsfall-Barrett scale (Horsfall et al., *Phytopathol.* 35:655 (1945)), in which 1 indicates no symptoms and 12 indicates symptoms on 100% of the plant. Results from a minimum of six plants per strain were averaged to obtain mean values of virulence.

*S. tuberosum* cv. Red Pontiac was used to evaluate virulence in potato. Plantlets were generated by micropropagating stem sections as previously described (Gamard et al., *Eur. J. Plant Pathol.* 101:519–525 (1995); Ishimaru et al., *Am. Pot. J.* 71:517–533 (1994)). After 21 to 28 days, plantlets were removed from tissue-culture medium. To promote bacterial entry, plantlet roots were trimmed aseptically to remove about one-third of the advancing root mass and immersed in a cell suspension of each strain. After soaking for 30 min, the plantlets were planted in soil. Six plantlets were included to calculate the mean severity of foliar wilt symptoms 12 weeks after inoculation, as described above for eggplant.

*C. michiganensis* subsp. *sepedonicus* strains Cs4, R5, Cs7, R14, and CIC31 were grown in YGM medium for 2 to 3 days until cultures reached an $OD_{650}$=2.0. Cells were removed by centrifugation (10,000×g for 15 min), and supernatant was sterilized by passage through 0.2 $\mu$m cellulose acetate filters (Schleicher & Schuell, Dassel, Germany). The sterile culture supernatant was concentrated with Centricon 10 mini-concentrators (Amicon, Beverly, Mass.) or Vivaspin 15-ml concentrators (Vivasciences, Binbrook Lincolnshire, England), having a cut-off size of 10 kDa, and then was desalted by washing with 3 volumes of 50 mM potassium phosphate buffer, pH 7.0. The resulting concentrated CCS was diluted with phosphate buffer to give a final concentration 3- to 15-fold higher than the original supernatant. Protein concentration was determined by the Biorad protein assay (Biorad, Hercules, Calif.).

To test specific activities of elicitor preparations, *C. michiganensis* subsp. *sepedonicus* strains CIC31 (virulent) and Cs4 (non-pathogenic) were grown in 2 liters of YGM Medium (300 rpm at 26° C.) to an $OD_{650}$=2.0. Cells were removed by centrifugation, and the supernatant was filter sterilized as above. Phenylmethylsulfonyl fluoride (PMSF) was added to give a final concentration 0.5 mM. The supernatant was cooled to 4° C., and ammonium sulfate was added to give 40% saturation. After overnight precipitation at 4° C., the precipitated proteins were collected by centrifugation at 4° C. and 10,000×g for 15 min. The pellet was suspended in 30 ml of 50 mM potassium phosphate buffer, pH 7.0, and concentrated and desalted with Vivaspin 15-ml filters as described above for concentrated CCS. These preparations are infiltrated into tobacco leaves after diluting to appropriate concentrations.

Concentrated CCS (50×) from CIC31 and CS3NM was prepared as described above, except that the supernatants were resuspended in 20 mM Bis-Tris ("BT") buffer, pH 6.0. Samples (400 $\mu$l) were loaded onto a DEAE cellulose column that had been equilibrated with BT buffer (bed volume 1.5 ml), and the column was washed with 10 ml of BT buffer. Proteins were eluted with a sodium chloride step gradient in BT buffer, with 50 mM increments from 50 to 300 mM, a 500 mM step, and a final 950 mM step. The fractions collected were concentrated and washed with BT buffer with Vivaspin concentrators and resuspended to a final 400-$\mu$l volume. Extracellular polysaccharide concentrations were determined calorimetrically (Dubois et al., *Anal. Chem.* 28:350–356 (1958)). Protein was loaded onto sodium dodecyl sulfate-10% polyacrylamide gels (SDS- PAGE) (Ausubel et al., *Current Protocols in Molecular Biology*, vol. 2, John Wiley & Sons, New York (1995)), and silver stained (silver staining kit, protein, Pharmacia Biotech, Uppsala, Sweden) according to the manufacturer's instructions.

The gene encoding this hypersensitive response elicitor protein or polypeptide can be obtained by procedures well known in the art. The protein can be purified through conventional techniques such as chromatography or electrophoresis. The amino terminal sequence of the protein is determined and used to design degenerate oligonucleotides which are labelled and used as probes to screen a clone library. Sambrook et al., *Molecular Cloning: A Laboratory Manual*, Cold Spring Harbor Press, Cold Spring Harbor, N.Y. (1989), which is hereby incorporated by reference. Plasmid DNA is isolated and sequenced from clones which hybridize to the amino terminal probe. The sequence of the DNA molecule can be determined using either chemical (Maxam et al., *Proc. Natl. Acad. Sci. USA*, 74:560 (1977), which is hereby incorporated by reference ) or enzymatic (Sanger, et al., *Proc. Natl. Acad. Sci. USA*, 74:5463 (1977), which is hereby incorporated by reference) methods.

Fragments of the above hypersensitive response elicitor polypeptide or protein are encompassed by the present invention.

Suitable fragments can be produced by several means. In the first, subclones of the gene encoding the elicitor protein of the present invention are produced by conventional molecular genetic manipulation by subcloning gene fragments. The subclones then are expressed in vitro or in vivo in bacterial cells to yield a smaller protein or peptide that can be tested for elicitor activity according to the procedure described below.

As an alternative, fragments of an elicitor protein can be produced by digestion of a full-length elicitor protein with proteolytic enzymes like chymotrypsin or Staphylococcus proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, differential pressure, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/- or KS+/- (see "Stratagene Cloning Systems" Catalog (1993) from Stratagene, La Jolla, Calif, which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus);

and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention relates to methods of imparting disease resistance to plants, enhancing plant growth, and/or effecting insect control for plants. These methods involve applying a hypersensitive response elicitor polypeptide or protein in a non-infectious form to all or part of a plant or a plant seed under conditions where the polypeptide or protein contacts all or part of the cells of the plant or plant seed. Alternatively, the hypersensitive response elicitor protein or polypeptide can be applied to plants such that seeds recovered from such plants themselves are able to impart disease resistance in plants, to enhance plant growth, and/or to effect insect control.

As an alternative to applying a hypersensitive response elicitor polypeptide or protein to plants or plant seeds in order to impart disease resistance in plants, to effect plant growth, and/or to control insects on the plants or plants grown from the seeds, transgenic plants or plant seeds can be utilized. When utilizing transgenic plants, this involves providing a transgenic plant transformed with a DNA molecule encoding a hypersensitive response elicitor polypeptide or protein and growing the plant under conditions effective to permit that DNA molecule to impart disease resistance to plants, to enhance plant growth, and/or to control insects. Alternatively, a transgenic plant seed transformed with a DNA molecule encoding a hypersensitive response elicitor polypeptide or protein can be provided and planted in soil. A plant is then propagated from the planted seed under conditions effective to permit that DNA molecule to impart disease resistance to plants, to enhance plant growth, and/or to control insects.

The embodiment of the present invention where the hypersensitive response elicitor polypeptide or protein is applied to the plant or plant seed can be carried out in a number of ways, including: 1) application of an isolated elicitor polypeptide or protein; 2) application of bacteria which do not cause disease and are transformed with genes encoding a hypersensitive response elicitor polypeptide or protein; and 3) application of bacteria which cause disease in some plant species (but not in those to which they are applied) and naturally contain a gene encoding the hypersensitive response elicitor polypeptide or protein.

In one embodiment of the present invention, the hypersensitive response elicitor polypeptide or protein of the present invention can be isolated from its bacterial source.

In other embodiments of the present invention, the hypersensitive response elicitor polypeptide or protein of the present invention can be applied to plants or plant seeds by applying bacteria containing genes encoding the hypersensitive response elicitor polypeptide or protein. Such bacteria must be capable of secreting or exporting the polypeptide or protein so that the elicitor can contact plant or plant seed cells. In these embodiments, the hypersensitive response elicitor polypeptide or protein is produced by the bacteria in planta or on seeds or just prior to introduction of the bacteria to the plants or plant seeds.

In one embodiment of the bacterial application mode of the present invention, the bacteria do not cause the disease and have been transformed (e.g., recombinantly) with genes encoding a hypersensitive response elicitor polypeptide or protein. For example, E. coli, which does not elicit a hypersensitive response in plants, can be transformed with genes encoding a hypersensitive response elicitor polypeptide or protein and then applied to plants. Bacterial species other than E. coli can also be used in this embodiment of the present invention.

In another embodiment of the bacterial application mode of the present invention, the bacteria do cause disease and naturally contain a gene encoding a hypersensitive response elicitor polypeptide or protein. Examples of such bacteria are noted above. However, in this embodiment, these bacteria are applied to plants or their seeds which are not susceptible to the disease carried by the bacteria.

The method of the present invention can be utilized to treat a wide variety of plants or their seeds to impart disease resistance, enhance growth, and/or control insects. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are: Arabidopsis thaliana, Saintpaulia, petunia, pelargonium, poinsettia, chrysanthemum, carnation, and zinnia.

With regard to the use of the hypersensitive response elicitor protein or polypeptide of the present invention in imparting disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: Tobacco mosaic virus and Tomato mosaic virus. Resistance, inter alia, to the following bacteria can also be imparted to plants in accordance with present invention: *Pseudomonas solancearum, Pseudomonas syringae* pv. *tabaci,* and *Xanthamonas campestris* pv. *pelargonii.* Plants can be made resistant, inter alia, to the following fungi by use of the method of the present invention: *Fusarium oxysporum* and *Phytophthora infestans.*

With regard to the use of the hypersensitive response elicitor protein or polypeptide of the present invention to enhance plant growth, various forms of plant growth enhancement or promotion can be achieved. This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

Another aspect of the present invention is directed to effecting any form of insect control for plants. For example, insect control according to the present invention encompasses preventing insects from contacting plants to which the hypersensitive response elicitor has been applied, preventing direct insect damage to plants by feeding injury, causing insects to depart from such plants, killing insects proximate to such plants, interfering with insect larval feeding on such plants, preventing insects from colonizing host plants, preventing colonizing insects from releasing phytotoxins, etc. The present invention also prevents subsequent disease damage to plants resulting from insect infection.

The present invention is effective against a wide variety of insects. European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, and tomato pinworm. Collectively, this group of insect pests represents the most economically important group of pests for vegetable production worldwide.

The method of the present invention involving application of the hypersensitive response elicitor polypeptide or protein can be carried out through a variety of procedures when all or part of the plant is treated, including leaves, stems, roots, propagules (e.g., cuttings), etc. This may (but need not) involve infiltration of the hypersensitive response elicitor polypeptide or protein into the plant. Suitable application methods include topical applications, such as high or low pressure spraying, as well as injection and leaf abrasion proximate to when elicitor application takes place. When treating plant seeds, in accordance with the application embodiment of the present invention, the hypersensitive response elicitor protein or polypeptide can be applied by topical procedures, such as low or high pressure spraying, coating, or immersion, as well as by injection. Other suitable application procedures can be envisioned by those skilled in the art provided they are able to effect contact of the hypersensitive response elicitor polypeptide or protein with cells of the plant or plant seed. Once treated with the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the hypersensitive response elicitor protein or polypeptide to impart disease resistance to plants, to enhance plant growth, and/or to control insects on the plants.

The hypersensitive response elicitor polypeptide or protein can be applied to plants or plant seeds in accordance with the present invention alone or in a mixture with other materials. Alternatively, the hypersensitive response elicitor polypeptide or protein can be applied separately to plants with other materials being applied at different times.

A composition suitable for treating plants or plant seeds in accordance with the application embodiment of the present invention contains a hypersensitive response elicitor polypeptide or protein in a carrier. Suitable carriers include water, aqueous solutions, slurries, or dry powders. In this embodiment, the composition contains greater than 500 nM hypersensitive response elicitor polypeptide or protein.

Although not required, this composition may contain additional additives including fertilizer, insecticide, fungicide, nematacide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response elicitor polypeptide or protein can be applied to plant seeds with other conventional seed formulation and treatment materials, including clays and polysaccharides.

In the alternative embodiment of the present invention involving the use of transgenic plants and transgenic seeds, a hypersensitive response elicitor polypeptide or protein need not be applied topically to the plants or seeds. Instead, transgenic plants transformed with a DNA molecule encoding a hypersensitive response elicitor polypeptide or protein are produced according to procedures well known in the art The vector described above can be microinjected directly into plant cells by use of micropipettes to transfer mechanically the recombinant DNA. Crossway, *Mol. Gen. Genetics,* 202:179–85 (1985), which is hereby incorporated by reference. The genetic material may also be transferred into the plant cell using polyethylene glycol. Krens, et al., *Nature,* 296:72–74 (1982), which is hereby incorporated by reference.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies. Fraley, et al., *Proc. Natl. Acad. Sci. USA,* 79:1859–63 (1982), which is hereby incorporated by reference.

The DNA molecule may also be introduced into the plant cells by electroporation. Fromm et al., *Proc. Natl. Acad. Sci. USA,* 82:5824 (1985), which is hereby incorporated by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science,* 237:1176–83 (1987), which is hereby incorporated by reference.

After transformation, the transformed plant cells must be regenerated.

Plant regeneration from cultured protoplasts is described in Evans et al., *Handbook of Plant Cell Cultures Vol.* 1: (MacMillan Publishing Co., New York, 1983); and Vasil I.R. (ed.), *Cell Culture and Somatic Cell Genetics of Plants,* Acad. Press, Orlando, Vol. I, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the hypersensitive response elicitor resulting in disease resistance, enhanced plant growth, and/or control of insects on the plant. Alternatively, transgenic seeds are recovered from the transgenic plants. These seeds can then be planted in the soil and cultivated using conventional procedures to produce transgenic plants. The transgenic plants are propagated from the planted transgenic seeds under conditions effective to impart disease resistance to plants, to enhance plant growth, and/or to control insects. While not wishing to be bound by theory, such disease resistance, growth enhancement, and/or insect control may be RNA mediated or may result from expression of the elicitor polypeptide or protein.

When transgenic plants and plant seeds are used in accordance with the present invention, they additionally can be treated with the same materials as are used to treat the plants and seeds to which a hypersensitive response elicitor polypeptide or protein is applied. These other materials, including hypersensitive response elicitors, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the hypersensitive response elicitor to impart disease resistance, enhance growth, and/or control insects. Such plants may also be treated with conventional plant treatment agents (e.g., insecticides, fertilizers, etc.).

Although the invention has been described in detail for the purpose of illustration, it is understood that such details are solely for that purpose and that variations can be made therein by those skilled in the art without departing from the spirit of the scope of the invention which is defined by the following claims.

What is claimed:

1. A method of imparting disease resistance to plants comprising:

applying a hypersensitive response elicitor protein or polypeptide from a virulent *Clavibacter michiganensis* strain, in a non-infectious form, to a plant or plant seed under conditions where the protein or polypeptide contacts the cells of the plants or the plant seeds and imparts disease resistance.

2. A method according to claim 1, wherein said protein or polypeptide is applied to a plant.

3. A method according to claim 1, wherein said protein or polypeptide is applied to plant seeds and, said method further comprises:

planting the seeds treated with the hypersensitive response elicitor in natural or artificial soil and propagating plants from the seeds planted in the soil.

4. A method according to claim 1, wherein the virulent *Clavibacter michiganensis* strain is *Clavibacter michiganensis* subsp. *sepedonicus*.

5. A method of enhancing plant growth comprising:

applying a hypersensitive response elicitor protein or polypeptide from a virulent *Clavibacter michiganensis* strain, in a non-infectious form, to a plant or plant seed under conditions where the protein or polypeptide contacts the cells of the plants or the plant seeds and enhances plant growth.

6. A method according to claim 5, wherein said protein or polypeptide is applied to a plant.

7. A method according to claim 5, wherein said protein or polypeptide is applied to plant seeds and, said method further comprises:

planting the seeds treated with the hypersensitive response elicitor in natural or artificial soil and propagating plants from the seeds planted in the soil.

8. A method according to claim 5 wherein the virulent *Clavibacter michiganensis* strain is *Clavibacter michiganensis* subsp. *sepedonicus*.

9. A method of insect control for plants comprising:

applying a hypersensitive response elicitor protein or polypeptide from a virulent *Clavibacter michiganensis* strain, in a non-infectious form, to a plant or plant seed under conditions where the protein or polypeptide contacts the cells of the plants or the plant seeds and controls insects.

10. A method according to claim 9, wherein said protein or polypeptide is applied to a plant.

11. A method according to claim 9, wherein said protein or polypeptide is applied to plant seeds and, said method further comprises:

planting the seeds treated with the hypersensitive response elicitor in natural or artificial soil and propagating plants from the seeds planted in the soil.

12. A method according to claim 9, wherein the virulent *Clavibacter michiganensis* strain is *Clavibacter michiganensis* subsp. *sepedonicus*.

* * * * *